(12) United States Patent
Makinson et al.

(10) Patent No.: US 8,245,710 B2
(45) Date of Patent: *Aug. 21, 2012

(54) APPARATUS FOR DELIVERING HUMIDIFIED GASES

(75) Inventors: Ian Douglas Makinson, Auckland (NZ); Martin P. F. Kramer, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 847 days.

This patent is subject to a terminal disclaimer.

(21) Appl. No.: 10/566,109

(22) PCT Filed: Jul. 27, 2004

(86) PCT No.: PCT/NZ2004/000166
§ 371 (c)(1),
(2), (4) Date: Apr. 26, 2006

(87) PCT Pub. No.: WO2005/011785
PCT Pub. Date: Feb. 10, 2005

(65) Prior Publication Data
US 2006/0272639 A1    Dec. 7, 2006

(30) Foreign Application Priority Data
Aug. 1, 2003  (NZ) .................................. 527381

(51) Int. Cl.
*A61M 15/00* (2006.01)
*A61M 16/00* (2006.01)
(52) U.S. Cl. ......... 128/204.14; 128/204.17; 128/203.16; 128/203.17; 128/203.26; 128/204.18
(58) Field of Classification Search ............ 128/200.24, 128/203.16, 202.27, 203.17, 203.26, 204.17, 128/204.18, 204.14; 55/503; 96/371; 392/386–406; 261/142, DIG. 65, 119.1, DIG. 46, 130
See application file for complete search history.

(56) References Cited

U.S. PATENT DOCUMENTS

| | | | | |
|---|---|---|---|---|
| 4,003,967 A | * | 1/1977 | Potvin | 261/30 |
| 5,231,979 A | * | 8/1993 | Rose et al. | 128/204.14 |
| 5,460,172 A | * | 10/1995 | Eckerbom et al. | 128/201.13 |
| 5,564,415 A | * | 10/1996 | Dobson et al. | 128/204.14 |
| 5,943,473 A | | 8/1999 | Levine | |

(Continued)

FOREIGN PATENT DOCUMENTS
AU        200065475        4/2001
(Continued)

*Primary Examiner* — Justine Yu
*Assistant Examiner* — Colin W Stuart
(74) *Attorney, Agent, or Firm* — Knobbe, Martens, Olson & Bear, LLP

(57) ABSTRACT

An apparatus (1) for use humidified gases delivery treatment comprising a housing, a humidifier, and a chamber heating base connected to said housing, said housing includes a pressurized gases supply, a humidifier engagement (17), a pressurized gases outlet (4), a humidified gases return (7), and a patient outlet (9), said humidifier includes a humidification chamber (2) having a base, a humidifier inlet (5), a humidifier outlet (6) and said chamber is engagable with said humidifier engagement (17) via a single motion, and said single motion of engagement urges the base of said humidification chamber adjacent and in contact with said chamber heating base and makes a first fluid connection between said pressurized gases outlet (4) and said humidifier inlet (5), and makes a second fluid connection between said humidified gases return (7) and said humidifier outlet (6), with said first and second fluid connections being made in the direction of said single motion.

14 Claims, 4 Drawing Sheets

U.S. PATENT DOCUMENTS

| | | | | |
|---|---|---|---|---|
| 5,992,413 | A * | 11/1999 | Martin et al. | 128/201.13 |
| 6,033,455 | A * | 3/2000 | Kurashima | 55/497 |
| 6,363,930 | B1 * | 4/2002 | Clawson et al. | 128/201.13 |
| 6,367,472 | B1 * | 4/2002 | Koch | 128/203.12 |
| 6,397,841 | B1 * | 6/2002 | Kenyon et al. | 128/202.27 |
| 6,398,197 | B1 * | 6/2002 | Dickinson et al. | 261/141 |
| 6,516,798 | B1 * | 2/2003 | Davies | 128/201.13 |
| 6,554,260 | B1 * | 4/2003 | Lipscombe et al. | 261/142 |
| 6,718,974 | B1 * | 4/2004 | Moberg | 128/204.14 |
| 6,953,354 | B2 * | 10/2005 | Edirisuriya et al. | 439/191 |
| 7,096,864 | B1 * | 8/2006 | Mayer et al. | 128/202.27 |
| 7,111,624 | B2 * | 9/2006 | Thudor et al. | 128/203.16 |
| 2002/0017302 | A1 * | 2/2002 | Fukunaga et al. | 128/207.14 |
| 2003/0070544 | A1 * | 4/2003 | Mulvaney et al. | 95/25 |
| 2006/0237012 | A1 * | 10/2006 | Thudor et al. | 128/203.16 |

FOREIGN PATENT DOCUMENTS

| | | |
|---|---|---|
| DE | 10226160 * | 6/2002 |
| EP | 0533644 | 12/1996 |
| EP | 1369141 | 12/2003 |
| WO | WO98/57691 | 12/1998 |
| WO | WO01/10489 | 8/2000 |
| WO | WO 0232486 A1 * | 4/2002 |
| WO | WO2004/026382 | 4/2004 |

* cited by examiner

APPARATUS FOR DELIVERING HUMIDIFIED GASES

BACKGROUND TO THE INVENTION

1. Field of the Invention

The present invention relates to apparatus for delivering humidified gases. In particular it relates to a humidifier arrangement for use in providing respiratory assistance to patients, for example in consumer Continuous Positive Airway Pressure (CPAP) delivery devices.

2. Summary of the Prior Art

Humidification systems are known which include a heater base and a disposable humidifier chamber which is fitted onto the heater base and within which a supply of water can be heated by the heater base. Air enters the humidifier chamber through an inlet air port in the roof of the chamber where it is humidified by the evaporation of water from the water supply before leaving the chamber through an exit port in the roof of the humidifier chamber.

Humidifier chambers of this type are also now used in compact and portable ventilation machines, for example machines intended for the home treatment of obstructive sleep apnoea (CPAP machines). Where the humidifier base is adapted for use with slide-on humidifier chambers, and the connection of the chamber to the machine is accomplished with a single sliding movement, the inlet air port is provided horizontally through the side of the chamber. Air enters the humidifier chamber through the inlet air port and the humidified air leaves the humidifier chamber into a breathing conduit through an exit port in the top of the humidifier chamber.

A disadvantage of these configurations is the need to disconnect the patient breathing conduit from the top of the humidifying chamber in a separate operation before removal of the chamber for the purpose of refilling. A further disadvantage of these configurations is that separate electrical wiring connections are required to make use of a heated respiratory conduit. Furthermore, in configurations such as these any contaminants or bacteria that enter the machine, such as a CPAP delivery to the humidifier chamber.

SUMMARY OF THE INVENTION

It is an object of the present invention to provide an apparatus for delivering humidified gases which at least goes some way towards overcoming the above disadvantages or which will at least provide the public with a useful choice.

An apparatus for use in humidified gases delivery treatment comprising:
a housing,
a pressurised gases supply within said housing,
a pressurised gases outlet in said housing in fluid connection with said pressurised gases supply and adapted to make fluid connection with an inlet of a humidifier in order to provide gases flow to a said humidifier, and
filter means on or over said inlet of said humidifier to filter said gases entering said humidifier.

Preferably said apparatus further comprises a humidified gases return in said housing, adapted to make fluid connection with an outlet of a said humidifier in order to receive humidified gases from said humidifier, and
a patient outlet in said housing, in fluid connection with said humidified gases return in order to receive humidified gases from said humidified gases return and provide humidified gases to said patient outlet, said patient outlet being in fluid connection with or adapted to make fluid connection with a breathing conduit for delivery of humidified gases to a patient.

Preferably said humidifier is a heatable water chamber, and said apparatus includes,
a chamber heating means connected to said housing and, said housing includes a humidifier engagement locating a said humidifier adjacent said chamber heating means, said chamber heating means adapted to vaporise liquid water in said water chamber in order to provide water vapour to said gases flow passing through said water chamber.

Preferably said humidification chamber has a base and said chamber is engagable with said humidifier engagement via a single motion, and said single motion of engagement urges the base of said humidification chamber adjacent and in contact with said chamber heating means and makes a first fluid connection between said pressurised gases outlet and said humidifier inlet, and makes a second fluid connection between said humidified gases return and said humidifier outlet, with said first and second fluid connections being made in the direction of said single motion.

Preferably said patient outlet includes a connector for receiving a breathing hose and at least one auxiliary electrical connection plug or socket or pneumatic connection plug or port, for a simultaneous connection when connecting a breathing circuit having complementary electrical and pneumatic connectors.

A humidifier chamber for use with a gases humidification apparatus comprising:
a container, with a surrounding wall and top, and an open bottom,
a heat conductive base enclosing said open bottom of said container,
a gases inlet to said container,
a gases outlet to said container, and
filter means on or over said inlet to said container to filter said gases to said container.

Preferably said humidification chamber further comprises a first elongate flow tube extending into said humidifier container from the inner periphery of said gases inlet and,
a second elongate flow tube extending into said humidifier container from the inner periphery of said gases outlet,
said first and said second flow tubes being substantially parallel to each other, and substantially parallel to said base of said chamber, and
said gases inlet and said gases outlet facing the same direction, a preferred insertion direction, and
said preferred insertion direction is substantially parallel to the said base of said chamber, such that
said humidifier chamber may make operable engagement with a heater base in a single motion,
and fluid connections with said gases outlet and said gases inlet, being also made in said single motion.

Preferably said filter means includes a framework substantially supporting a filter material, said framework being shaped to fit the internal shape of said inlet, and including means to lock said filter means in place in said inlet.

Preferably said filter material is interposed between the structural members of said framework.

Preferably said locking means being a friction fit between said filter means and said inlet.

Preferably said second flow tube includes an air bleed orifice, said air bleed orifice being located in the top of said second elongate flow tube, and located toward the end of the elongate flow tube adjacent said gases outlet.

Preferably said gases inlet and said gases outlet of said humidifier chamber are each a female port, and said humidifier chamber is generally cylindrical, and said female ports open out to the cylindrical surface adjacent the top of the cylindrical wall.

DETAILED DESCRIPTION OF THE PREFERRED EMBODIMENTS

The present invention provides improvements in the delivery of humidified gases delivery treatment such as, CPAP ventilation therapy. The device described is an integrated humidifier and CPAP machine, where the air supplied to the humidifier chamber is filtered before entering the chamber. The combined humidifier and CPAP device is manufactured and assembled in such a way that the humidifier chamber may be removed for cleaning, replacement or refilling easily and quickly, and when the humidifier chamber is separated from the CPAP machine, the filter may also be removed for cleaning or replacement quickly and easily. In other forms of the present invention the humidifier and filter may be used with other devices, for example a blower that merely provides oxygen therapy.

Figure 1:
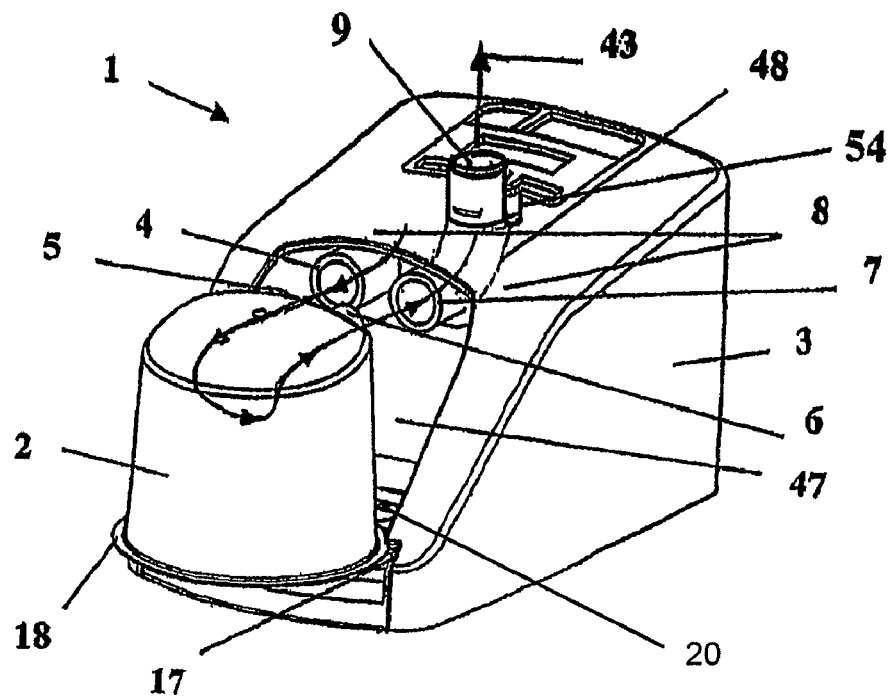
FIG. 1 is a perspective view of a water chamber and Continuous Positive Airways Pressure (CPAP) machine according to the first preferred embodiment of the present invention showing the water chamber 2 separated from the CPAP machine 1 and an arrow 43 indicating the path of air flow through the connection manifold of the CPAP machine and chamber.
Figure 2:
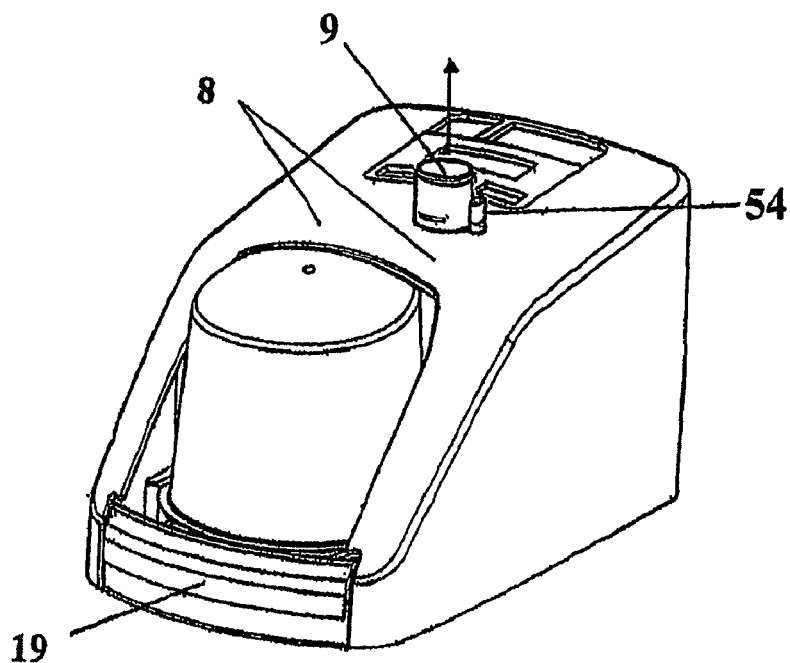
FIG. 2 is a perspective view of a water chamber and CPAP machine according to the first preferred embodiment of the present invention showing the water chamber 2 engaged with the CPAP machine 1 as in use and an arrow indicating the exit path of air flow through the conduit connection manifold 9.

Referring to FIGS. 1 and 2, a preferred embodiment of a CPAP machine and corresponding water chamber is shown that may be used with the filter of the present invention. A CPAP machine of a suitable type is described in co-pending NZ patent application No. 521446. A water chamber 2 having a gases inlet port 5 and gases outlet port 6 is shown with a portable CPAP machine 3, wherein the CPAP machine 3 is adapted to receive slide-on chambers and which makes connection to the gases inlet/outlet ports 5, 6 of the water chamber 2 through a connection manifold 8. This connection of the gases inlet port 5 and gases outlet port 6 is made to the connection manifold 8 of the CPAP machine 3 in the same slide-on motion. The connection manifold 8 also provides an auxiliary outlet connection port 9 suitable for receiving a flexible respiratory conduit (not shown) to deliver humidified air to a patient.

The CPAP machine 3 includes a heater base 20 in a chamber receiving bay 47 to heat the water chamber 2, and a securing means for securing the water chamber 2 to the CPAP machine 3. The securing means is provided by a securing latch 19 and a slot 17 around the periphery of the chamber receiving bay 47. The slot 17 co-operates with a flange 18 around the base of the water chamber 2 to secure the chamber 2 when in use. The securing latch 19 operates to prevent removal of the chamber 2 once it has been engaged. The securing means and connection manifold 8 are arranged with a parallel axis of operation such that connection of the chamber inlet port 5 and outlet port 6, to the connection manifold 8 is achieved as well as securing of the chamber into the CPAP machine in the same slide-on motion.

The latch 19, having a locking position and a release position, is biased toward the locking position which prevents removal of the chamber 2 from the CPAP machine 3. The front face of the latch is shaped such that during the single slide-on motion employed to fit the water chamber to the CPAP machine the flange 18 urges the securing latch 19 into the release position and allows the water chamber 2 to be properly fitted. Once the water chamber 2 is properly seated on the heater base (not shown) and the inlet 5 and outlet 6 are properly engaged with the connection manifold 8, the flange 18 and base of the chamber 2 will no longer be in contact with the securing latch 19. This allows the securing latch biasing means to urge the latch 19 into the locking position and prevents the water chamber 2 from being removed, as shown in FIG. 2.

Preferably the connection manifold 8 includes a passage 4 which receives gases flow from the integral CPAP blower, and directs it into the water chamber 2, as well as a passage 7 which directs airflow received via the water chamber outlet port 6, to the CPAP patient outlet port 9. The connection passage connecting the manifold inlet port 7, to the manifold patient outlet port 9 is shown in hidden detail 48 in FIG. 1. Preferably the connection manifold 8 of the present invention is removable to aid cleaning and/or sterilisation of the passages. In one preferred embodiment the above connection passages 4, 7 are internal to the connection manifold 8 as illustrated in FIGS. 1 and 2. In use, gases from the CPAP internal blower (not shown) exits the CPAP machine 3 through outlet port 4, and enters the chamber 2 through inlet port 5.

Figure 4:
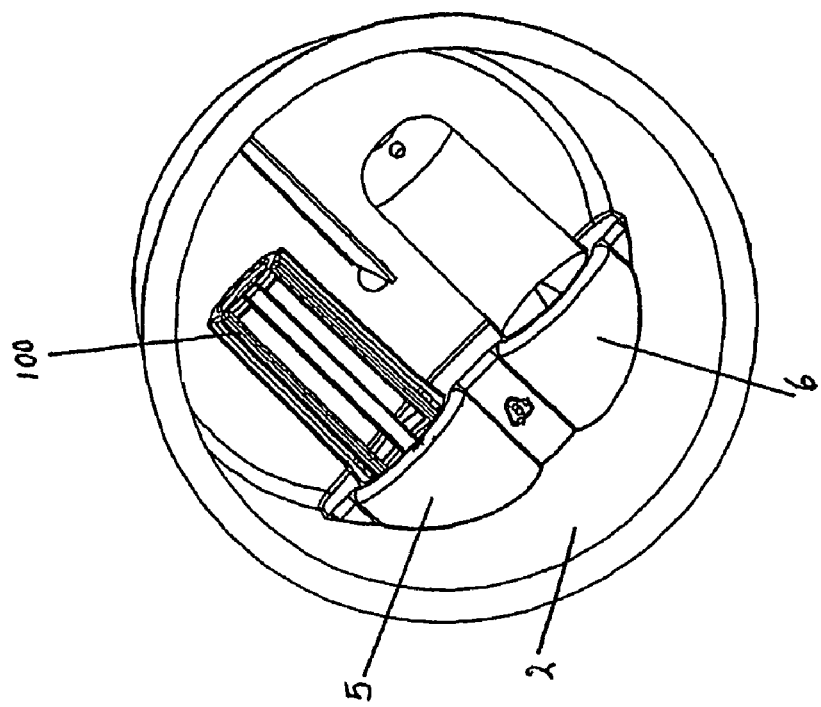
FIG. 4 is an underneath view of the water chamber of FIG. 3 including the filter of the present invention.
Figure 3:
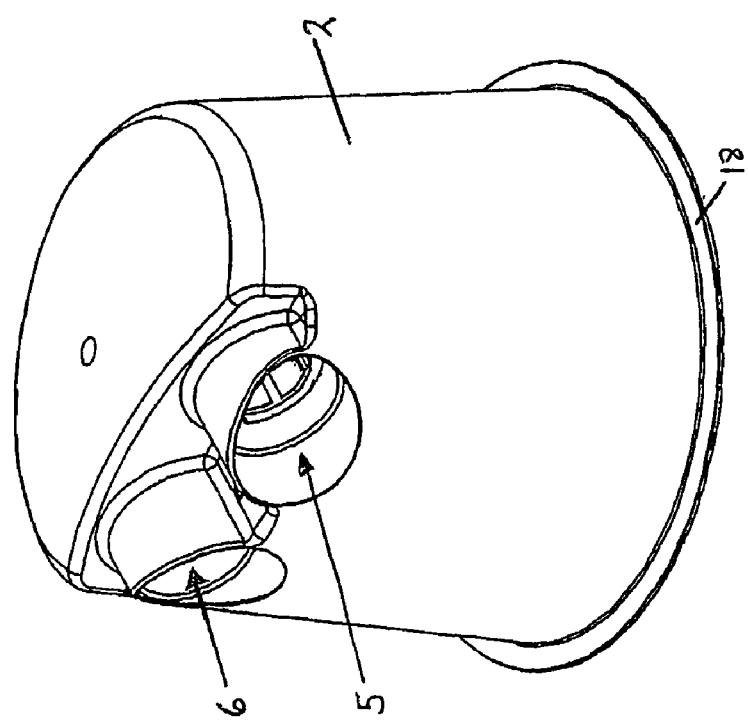
FIG. 3 is a perspective view of a water chamber for use with the filter of the present invention.
Figure 6:
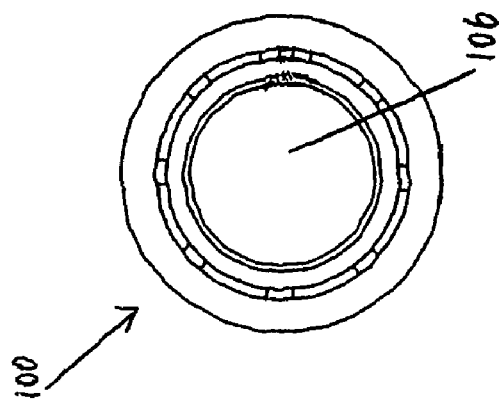
FIG. 6 is a front view of the filter frame of FIG. 5.
Figure 5:
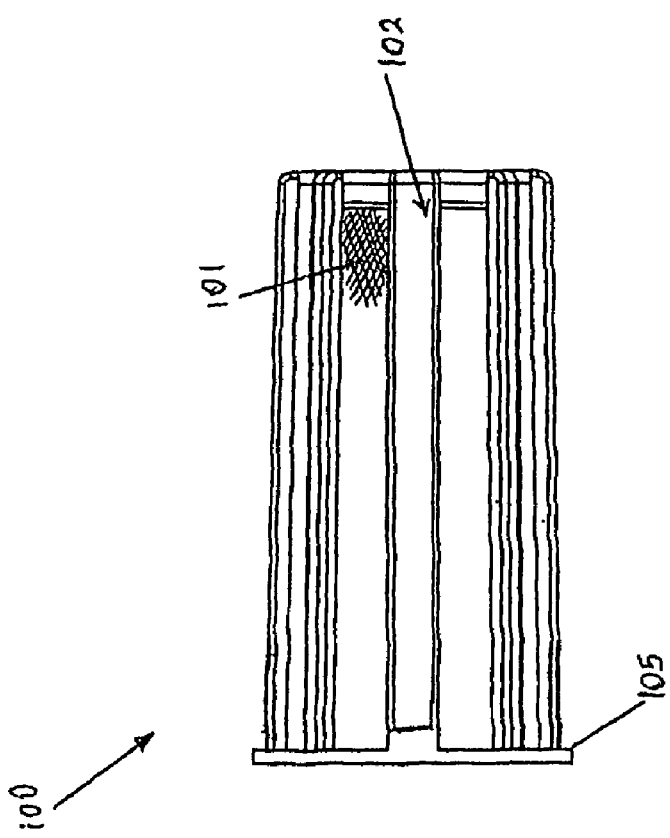
FIG. 5 is a side view of the filter frame.
Figure 7:
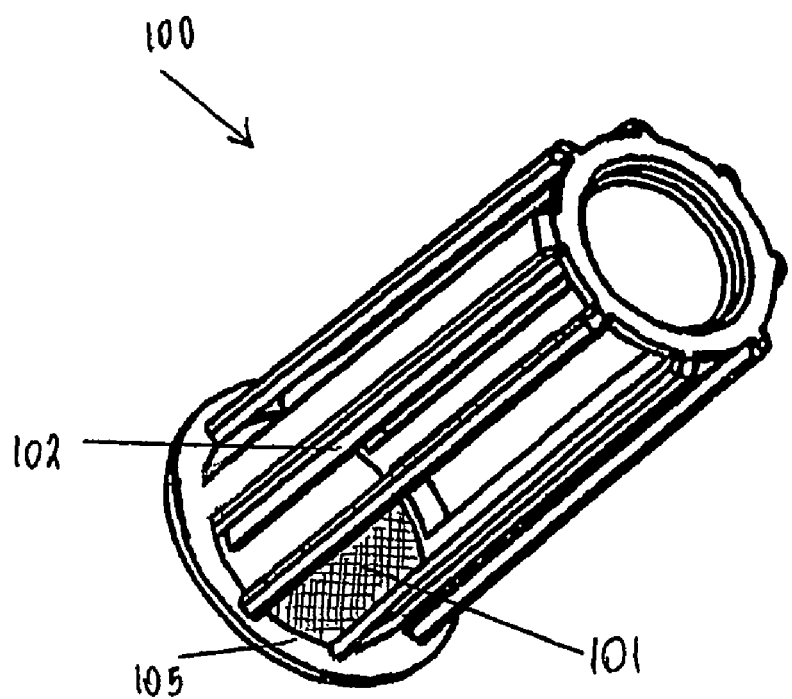
FIG. 7 is a first perspective view of the filter frame of FIG. 5.
Figure 8:
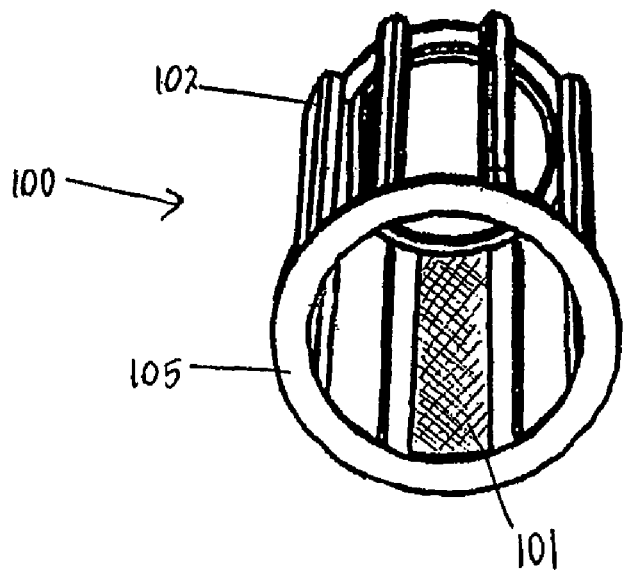
FIG. 8 is a second perspective view of the filter frame of FIG. 5.

Referring to FIGS. 1, 3 and 4, a disposable filter assembly 100 is removably attached to the inlet port 5, inside water chamber 2. In use, gases entering the chamber 2 pass through the filter assembly 100 before entering the chamber 2. Air entering the chamber 2 is humidified by the evaporation of water from the water source in the bottom of the chamber 2 before leaving the chamber 2 through the patient outlet port 6. Humidified air from the outlet port 6 is received into the connection manifold 8 of the CPAP machine 3 via the inlet port 7. The connection manifold (see FIG. 1) directs air from the water chamber to the outlet port 9 which is adapted to connect with a flexible conduit connector (not shown) for delivery to a patient. An advantage obtained from the breathing conduit connection 9 being located on the body of the CPAP machine 3 and not connected to the top of the water chamber 2 directly, is that complete connection or disconnection of the water chamber 2 from the CPAP machine 3 can be achieved with a single slide-on or slide-off motion. This feature makes removal of the water chamber 2 for refilling or cleaning or replacing, and removal of the disposable filter assembly 100 from water chamber 2, for cleaning or replacing, considerably simpler.

A further advantage is obtained when additional electrical or pneumatic connections are required. The use of heated conduits requires electrical wiring connectors between the conduit and humidified air source while an additional pneumatic connection 54 may be used for pressure feedback or measurement. In the present invention the connector which includes an additional electrical and/or pneumatic connection for the conduit is integral to the connection manifold 8 of the CPAP machine 3 and therefore allows the disposable water chamber 2 to remain as simple as possible.

The gases entering the humidifier chamber is filtered in order to sterilise it. This is achieved by passing the gases from the CPAP machine 3 through a filter assembly 100 before it enters the humidification chamber 2.

The filter assembly consists of an inlet opening, a connection mechanism for attaching the inlet opening to the gases supplied from the CPAP machine, a filter gauze, and a support framework. In operation, all gases entering the filter assembly passes through the inlet opening.

In a preferred embodiment, with reference to FIGS. 3 to 8, gases enter the filter assembly 100 through the inlet opening 106, inlet opening 106 being substantially circular, and sized to match the inlet port 5 of the humidifier chamber 2.

The filter assembly inlet opening 106 is connected to the gases supply from the CPAP machine 3 via a connection mechanism. The connection mechanism is designed in such a way that the filter assembly 100 may be quickly and easily connected or disconnected, for replacement or cleaning. An airtight seal is formed around the perimeter of the connection, so that all air routed from the CPAP machine 3 passes through the inlet opening 106 into the filter assembly 100.

In a preferred embodiment, the filter assembly inlet opening 106 is bounded by a lip 105 which mates by friction press-fitting with a complimentary lip or recess (not shown) on the inlet port 5, in order to form an airtight seal between the perimeters of the filter assembly inlet opening 106 and the inlet port 5. The filter assembly 100 can be removed or replaced by removing the base 18 of the chamber 2 and, for example, pushing, pressing or pulling the filter assembly 100 from the inlet port 5 of the humidification chamber 2.

All gases entering the filter assembly 100 must then pass through the filter gauze in order to exit into the humidifier chamber 2. The gauze material is selected from a range of materials well known from the prior art that will sterilise air that passes through the gauze. The material is also selected so that at least a minimum required volume of air will pass through the filter over a set period of time, bearing in mind the normal operating pressures of the CPAP machine.

In a preferred embodiment, the filter gauze 101 is made of ELECTRET™, which is a commonly used medical grade synthetic material, which filters an airstream using electrostatic charges. The gauze material 101 is shaped and held in place by the support framework, which holds the filter gauze 101 in place securely and tautly. The filter gauze 101 is attached to the support framework in such a fashion that all air entering the filter assembly 100 enters through the filter assembly inlet opening 106, and will pass through the filter gauze 101 before entering chamber 2. The filter support framework is shaped and sized so that at least a minimum required surface area of the filter gauze 101 is presented to the airstream entering the filter assembly 100 through the inlet opening 106. This allows at least a minimum required volume of air to pass through the filter assembly 100, the total volume depending on the filter gauze material selected, the time interval, and the outlet pressure of the CPAP machine 3.

In a preferred embodiment, the support framework is a hollow cylindrical cage 102, open at one end. The open end of the cylindrical cage 102 acts as the inlet opening 106. The connection mechanism 105 is located on the circumference of this open end of cylindrical cage 102. The filter gauze 101 is securely attached to the inside of the cylindrical cage 102 in such a way that one layer of gauze covers all the gaps between the structural members of cage 102 except inlet opening 106.

In a preferred embodiment, the support frame 102, inlet opening 106 and connection mechanism 105 are all constructed through one injection moulding operation. A pre-cut and shaped single-piece filter gauze 101 is added to the framework thus created, and in the preferred embodiment is attached in place by overmoulding, although it may be glued, clipped, or held in place by any other suitable attachment means which holds the gauze 101 in place and provides a seal, with no gaps between the gauze 101 and the support frame 102.

In a preferred embodiment the inlet opening 106 of the filter assembly 100 is removably attached via the connection mechanism 105 to inlet port 5, on the inside of humidifier chamber 2. The filter assembly 100 is shaped and sized so that once the connection between the inlet port 5 and the connection mechanism 105 is made, the filter assembly 100 is held entirely within chamber 2, and when the combined CPAP/humidifier device 3 is in the normal operating position, there will be no contact between the filter assembly 100 and the contents of humidifier chamber 2.

It will be readily appreciated that the construction of the filter assembly as described is simple to manufacture. Consequently a water chamber including a filter according to the present invention is, while providing significant advantages, not significantly more expensive than existing chambers. Also, the filter assembly of the present invention prevents bacteria, viruses or the like from entering into the inner workings of the CPAP machine, preventing contamination and allowing it to be reused for different a patient.

The invention claimed is:

1. An apparatus for use in humidified gases delivery treatment comprising:
   a housing,
   a pressurised gases supply within said housing,
   a pressurised gases outlet in said housing in fluid connection with said pressurised gases supply and adapted to make fluid connection with an inlet of a humidifier in order to provide pressurised gases flow to said humidifier, said humidifier comprising a heatable water chamber, and
   a removable filter in said inlet of said humidifier and downstream of said pressurised gases supply, said removable filter extending through said inlet into said heatable water chamber.

2. An apparatus according to claim 1 further comprising a humidified gases return in said housing, adapted to make fluid connection with an outlet of said humidifier in order to receive humidified gases from said humidifier,
   and a patient outlet in said housing, in fluid connection with said humidified gases return in order to receive humidified gases from said humidified gases return and provide humidified gases to said patient outlet, said patient outlet being in fluid connection with or adapted to make fluid connection with a breathing conduit for delivery of humidified gases to a patient.

3. An apparatus according to claim 1 or 2 wherein said apparatus includes a chamber heating base connected to said housing and said housing includes a humidifier engagement locating said heatable water chamber adjacent said chamber heating base, said chamber heating base adapted to vaporise liquid water in said heatable water chamber in order to provide water vapour to said gases flow passing through said heatable water chamber.

4. An apparatus according to claim 3 wherein said heatable water chamber has a base and said heatable water chamber is engagable with said humidifier engagement via a single motion, and said single motion of engagement urges a base of said heatable water chamber adjacent and in contact with said chamber heating base and makes a first fluid connection between said pressurised gases outlet and said inlet of said humidifier, and makes a second fluid connection between said humidified gases return and said outlet of said humidifier, with said first and second fluid connections being made in the direction of said single motion.

5. An apparatus according claim 2 wherein said patient outlet includes a connector for receiving a breathing hose and at least one auxiliary electrical connection plug or socket or pneumatic connection plug or port, for a simultaneous connection when connecting said breathing hose.

6. A humidifier chamber for use with a gases humidification apparatus comprising:
   a container, with a surrounding wall and top, and an open bottom,
   a heat conductive base enclosing said open bottom of said container,
   a gases inlet to said container adapted to receive pressurised gases for humidification from a pressurised gases supply,
   a gases outlet from said container, and
   a removable filter positioned within and extending through said gases inlet into said container and downstream to said pressurised gases supply, said filter positioned such that said filter can filter pressurised gases supplied to said container.

7. A humidifier chamber according to claim 6 further comprising a first elongate flow tube extending into said container from an inner periphery of said gases inlet and,
   a second elongate flow tube extending into said container from an inner periphery of said gases outlet,
   said first and said second flow tubes being substantially parallel to each other, and substantially parallel to said heat conductive base of said chamber,
   said gases inlet and said gases outlet facing the same direction, a preferred insertion direction,
   said preferred insertion direction being substantially parallel to said base of said chamber, such that said humidifier chamber may make operable engagement with a heater base in a single motion,
   and fluid connections with said gases outlet and said gases inlet being also made in said single motion.

8. A humidifier chamber according to claim 6 wherein said filter includes a framework substantially supporting a filter material, said framework being shaped to fit an internal shape of said gases inlet, and including means to lock said filter in place in said gases inlet.

9. A humidifier chamber according to claim 8 wherein said filter material is interposed between structural members of said framework.

10. A humidifier chamber according to claim 8 wherein said means to lock is a friction fit between said filter and said gases inlet.

11. A humidifier chamber according to claim 6 wherein said gases inlet and said gases outlet of said humidifier chamber are each a female port, and said humidifier chamber comprises a generally cylindrical wall, and said female ports open out to said generally cylindrical wall adjacent a top of said generally cylindrical wall.

12. An apparatus according to claim 1 wherein said removable filter is positioned such that said removable filter can filter pressurised gases entering said humidifier and protect said pressurised gases supply and said housing from contamination.

13. An apparatus according to claim 1 wherein said removable filter is positioned such that said removable filter can filter pressurised gases entering said humidifier and protect said humidifier from contamination.

14. An apparatus according to claim 1, wherein said removable filter and said heatable water chamber are detachable from said pressurised gases supply together.

* * * * *